(12) United States Patent
Aboul-Hosn et al.

(10) Patent No.: US 6,613,008 B2
(45) Date of Patent: Sep. 2, 2003

(54) INTEGRATED SYSTEM FOR CARDIOPULMONARY BYPASS AND RELATED METHODS

(75) Inventors: Walid Najib Aboul-Hosn, Fair Oaks, CA (US); Scott Youmans, Bothell, WA (US)

(73) Assignee: A-Med Systems, Inc., W. Sacramento, CA (US)

( * ) Notice: Subject to any disclaimer, the term of this patent is extended or adjusted under 35 U.S.C. 154(b) by 0 days.

(21) Appl. No.: 09/877,488

(22) Filed: Jun. 8, 2001

(65) Prior Publication Data

US 2002/0044889 A1 Apr. 18, 2002

Related U.S. Application Data

(60) Provisional application No. 60/211,713, filed on Jun. 13, 2000.

(51) Int. Cl.$^7$ .............................................. A61M 37/00
(52) U.S. Cl. ................ 604/5.01; 604/6.11; 604/6.14
(58) Field of Search ..................... 604/4.01, 5.01, 604/6.01, 6.15, 6.16, 6.14; 210/645, 252–262; 422/44; 128/849, 852

(56) References Cited

U.S. PATENT DOCUMENTS

| | | | |
|---|---|---|---|
| 4,664,103 A | 5/1987 | Martin et al. | |
| 5,021,048 A | 6/1991 | Buckholtz | |
| 5,074,316 A | 12/1991 | Dowdy | |
| 5,385,540 A | 1/1995 | Abbott et al. | |
| 5,423,769 A | 6/1995 | Jonkman et al. | |
| 5,573,502 A | 11/1996 | LeCocq et al. | |
| 5,702,358 A | 12/1997 | Witherspoon et al. | |
| 5,707,703 A | 1/1998 | Rothrum et al. | |
| 5,770,149 A | * 6/1998 | Raible | 422/46 |
| 5,840,070 A | 11/1998 | Wampler | |
| 5,849,005 A | * 12/1998 | Garrison et al. | 604/26 |
| 5,899,873 A | 5/1999 | Jones et al. | |
| 5,965,089 A | 10/1999 | Jarvik et al. | |
| 5,970,980 A | 10/1999 | Adair | |
| 6,123,725 A | 9/2000 | Aboul-Hosn | |
| 6,187,126 B1 | 2/2001 | Rothrum et al. | |
| 6,309,382 B1 | * 10/2001 | Garrison et al. | 604/26 |
| 6,387,323 B1 | * 5/2002 | Afzal et al. | 422/45 |

* cited by examiner

*Primary Examiner*—Edward K. Look
*Assistant Examiner*—John K. Fristoe, Jr.
(74) *Attorney, Agent, or Firm*—Ryan Kromholz & Manion, S.C.

(57) ABSTRACT

An improved cardiopulmonary bypass system which consolidates and miniaturizes the entire CPB circuit on an integrated panel or box-type structure capable of being positioned within (or closely adjacent to) the sterile surgical field.

5 Claims, 11 Drawing Sheets

INTEGRATED SYSTEM FOR CARDIOPULMONARY BYPASS AND RELATED METHODS

CROSS-REFERENCE TO RELATED APPLICATIONS

This application claims the benefit under Title 35, United States Code, §119(e) of U. S. Provision Application No. 60/211,713 filed on Jun. 13, 2000 entitled "Integrated System for Cardiopulmonary Bypass and Related Methods."

BACKGROUND OF THE INVENTION

I. Field of the Invention

The present invention relates generally to cardiopulmonary bypass systems. More particularly, the present invention is directed to an improved cardiopulmonary bypass system which consolidates and miniaturizes the entire CPB circuit on an integrated panel or box-type structure capable of being positioned within (or closely adjacent to) the sterile surgical field.

II. Discussion of the Prior Art

Cardiopulmonary bypass—mechanical bypass of the heart and lungs—is employed in both cardiovascular and cardiac surgery. A cardiopulmonary bypass circuit is composed of two primary technologies: mechanical circulation of blood during temporary heart arrest, and artificial oxygenation of blood while blood flow is excluded from the lungs. FIG. 1 illustrates a typical prior art CPB circuit 10 within a typical operating room setting. Blood is removed from the patient through use of a venous cannula 12 inserted into the inferior and superior vena cava using gravity or vacuum assisted venous drainage into a venous reservoir 14. The venous reservoir 14 often receives venous return in addition to field suction return (blood recovery via roller pump or vacuum activated suction wands). Alternatively, cell-washing technology may be employed prior to the return of blood to the patient. An arterial pump 16, typically a remote mounted roller or centrifugal style pump, pulls blood from the venous reservoir 14 and pushes the blood into an oxygenator 18. The arterial pump 16 is most often located on a heart lung machine 20, behind the main or assisting physician in the operating room, approximately 5 feet back from the patient table 21. Oxyhemoglobin is created in the oxygenator 18, most commonly through use of a porous hollow fiber capillary material with blood flowing around the fibers and oxygen flowing through the fibers. Pressure from the arterial pump 16 continues to move blood out the oxygenator 18 through an arterial filter 24. The arterial filter 24 serves as a final filter for possible air and particulate introduced through the circuit. Blood is returned to the patient via the arterial cannula 26, usually placed in the patient's aorta.

While generally helpful in performing various cardiovascular and cardiac surgical procedures, traditional CPB circuits suffer several significant drawbacks. A major disadvantage is that such traditional CPB systems require a relatively large amount of fluid (such as saline) to prime the CPB circuit. The high prime-volume is due to the fact that the components used in traditional CPB circuits are typically quite bulky and oftentimes disposed in a spread apart or non-consolidated fashion. The use of such high amounts of priming liquid is disadvantageous in that results in hemodilution of the patient's blood supply when the CPB circuit is coupled to the patient. Hemodilution is a paramount concern because it reduces the relative amounts of hematocrit (and hence hemoglobin) within the patient during such procedures, thereby reducing the blood's oxygen carrying capability. This is particularly troublesome in neonatal and pediatric cases, where the amount of prime-volume is typically quite large relative to the amount of blood within the patient. To combat hemodilution, it becomes necessary to cool the patient to thereby reduce the oxygen requirements and/or introduce additional blood into the patient to raise hematocrit levels, both of which are disadvantageous to the patient. Cooling the patient is disadvantageous because it causes the patient to be "on pump" for the very lengthy process of cooling down and warming up the patient, which is both costly and physically taxing on the patient. Infusing additional blood into the patient is disadvantageous in that it presents the risk of contaminating the patient with blood-born pathogens (such as HIV), as well as the possibility of rejection and adding significant costs to the overall procedure.

Another significant drawback of traditional CPB circuits is that, due to their bulky size and non-consolidated layout, the individual components forming the CPB circuit are typically located at a lower vertical level than the patient. This is disadvantageous in that air emboli generated by or disposed within the CPB circuit may migrate vertically upward within the CPB circuit and be introduced into the patient.

A still further drawback of traditional CPB circuits relates to their physical location within the operating room. Once again, due to their bulky nature and nonconsolidated layout, traditional CPB circuits are disposed well outside the sterile surgical field. Positioning the CPB circuit in this fashion requires the use of long lengths of surgical tubing to connect the patient to the CPB circuit. This increases the blood's exposure to foreign substances, well known to activate a system wide roster of plasma proteins and blood components designed to act locally in response to infection or injury.

A need exists for apparatus systems, methods and associated equipment to minimize and/or eliminate the aforementioned drawbacks of traditional CPB circuits. The present invention is directed at addressing this need.

SUMMARY OF THE INVENTION

The present invention solves the aforementioned drawbacks of the prior art by providing a cardiopulmonary bypass integration panel ("CPB integration panel") which consolidates and miniaturizes the complete CPB circuit such that it may be positioned within (or closely adjacent to) the sterile field. The CPB integration panel of the present invention may take the form of a panel, manifold or box-type structure designed to support or enclose one or more elements of the CPB circuit. These elements may include, but are not necessarily limited to, a blood pump, a cardioplegia pump, an oxygenator, a heat exchanger, venous and/or arterial reservoirs, and an arterial filter. The majority of these components are miniaturized relative to prior art offerings, including but not limited to the blood pump, the oxygenator, and the heat exchanger. One such miniaturized oxygenator, incorporating blood pump features, forms part of the present invention. The oxygenator of the present invention improves upon the prior art by decreasing the priming volume and utilizing less fiber to obtain proper oxygenation. Further, the oxygenator of the present invention provides a novel flow path, whereby the size of the oxygenator may be reduced without decreasing functionality of the oxygenator.

Component modularity is maintained for ease of component replacement should the need arise, such as by equipping the circuit components with quick-connect couplings. Ease of use is also facilitated by providing quick-connect couplings to quickly and easily couple the CPB integration panel to the venous and arterial cannulae employed to transport blood between the patient and the CPB integration panel. The CPB integration panel may be positioned to define the sterile/non-sterile field. In this regard, the CPB integration panel may have a sterile field drape or other sterile/non-sterile barrier directly integrated/attached into its structure through standard methods. When configured as a manifold or box-type structure, the CPB integration panel may house within its structure the various fluid communication conduits that extend between elements of the CPB circuit. The CPB integration panel may mount on an IV (standardized or custom) pole, bed rail mounted pole, or rest within the surgical field (e.g. directly on the surgical bed).

A cable-driven blood pump is preferably employed as the means of distributing blood throughout the CPB integration panel. The CPB integration panel may also include a passive reservoir or an active reservoir on the venous side. The CPB integration panel may be pre-packaged for easy deployment, including the ability to ship the entire circuit, up to the sterile side cannula connections pre-primed. The CPB integration panel is also developed for ease of priming including a quick-purge (CO2 purge connection) and quick-prime (vacuum connection for easy circuit prime) latch connections which can be easily attached/detached.

By and through these features, the CPB integration panel of the present invention represents a significant advancement over traditional CPB circuits found in the prior art. First, the CPB integration panel of the present invention boasts a dramatically reduced prime-volume relative to traditional CPB circuits, thereby reducing hemodilution and its associated drawbacks. This is particularly advantageous in neonatal and pediatric cases, not to mention adult cases. The CPB integration panel of the present invention may also be positioned at a higher vertical level than the patient, thereby minimizing the risk of introducing air emboli into the patient. The CPB integration panel of the present invention minimizes the blood's exposure to foreign surfaces, thereby reducing the risk of activating the blood's immuno-response system.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 1:
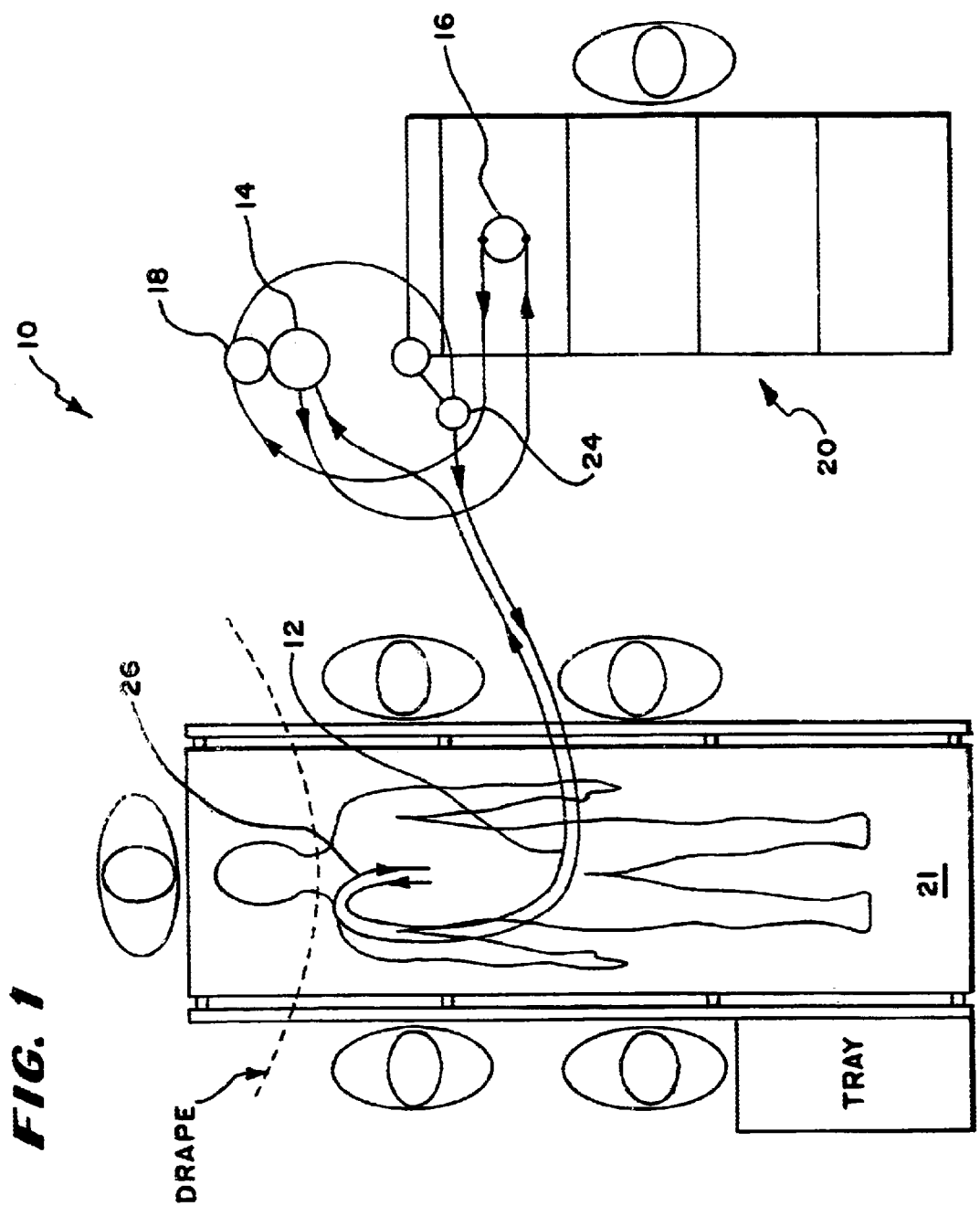
FIG. 1 is a top view of a prior art cardiopulmonary bypass (CPB) circuit employed within an operating room (OR) setting.
Figure 2:
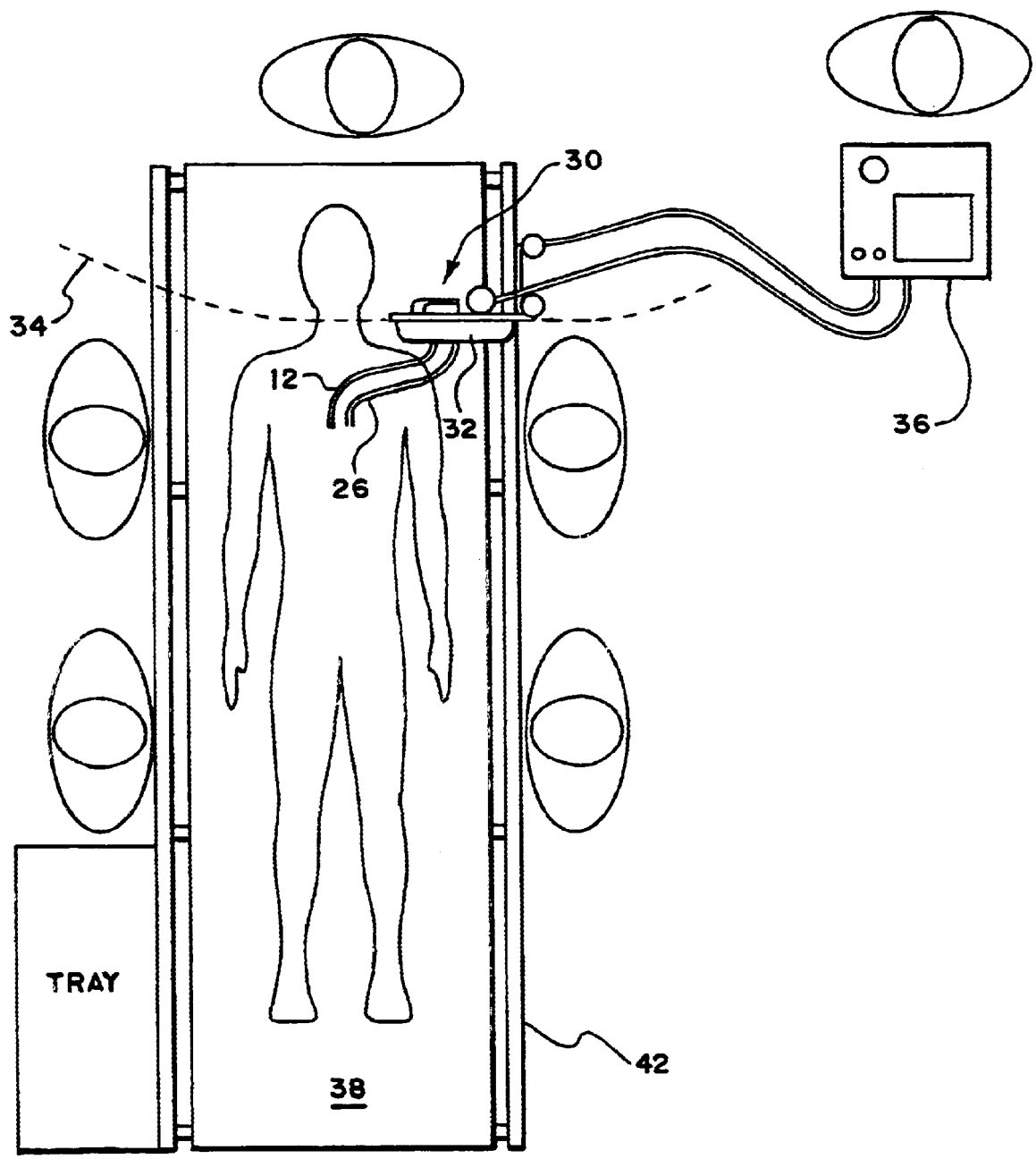
FIG. 2 is a top view of a cardiopulmonary bypass integration panel (CPB integration panel) according to one embodiment of the present invention employed within an OR setting.

Referring to FIG. 2, shown is a cardiopulmonary bypass integration panel 30 (CPB integration panel 30) of the present invention in use within an operating room setting. As will be described in greater detail below, the CPB integration panel 30 of the present invention comprises a panel, manifold or box-type structure 32 designed to support or enclose one or more elements of a traditional CPB circuit in a consolidated and miniaturized fashion. As is apparent, this consolidation and miniaturization provides the ability to position the CPB integration panel 30 quite near the patient. For example, the CPB integration panel 30 may be coupled to a sterile drape 34 and positioned on the surgical bed 38 (as shown) to define the actual sterile/non-sterile boundary (i.e. the non-sterile field is established above the patient's neck, while the sterile field is established below the patient's neck). Sterile drape 34 may comprise any number of commercially available drapes, as well as that shown and described in copending and commonly owned U.S. Pat. App. Ser. No. 09/729,740 filed Dec. 4, 2000 entitled "Surgical Drape and Panel Assembly" and claiming priority to U.S. Provisional Pat. App. No. 60/168,795 of the same title filed Dec. 2, 1999, the entire contents of which is hereby incorporated herein by reference. In addition to being able to define the sterile/non-sterile field, the CPB integration panel 30 of the present invention brings the entire CPB circuit to the patient. This advantageously reduces amount of prime-volume within the system (thereby minimizing hemodilution), as well as the amount of tubing required to couple the patient to the CPB integration panel 30 (thereby minimizing the risk of activating the blood's immuno-response system). A control console 36 is communicatively coupled to the CPB integration panel 30 to coordinate and control the operation of the various CPB circuit components. The CPB integration panel 30 of the present invention may take several forms, two of which are illustrated (by way) of example only) in FIGS. 3 and 4.

Figure 3:
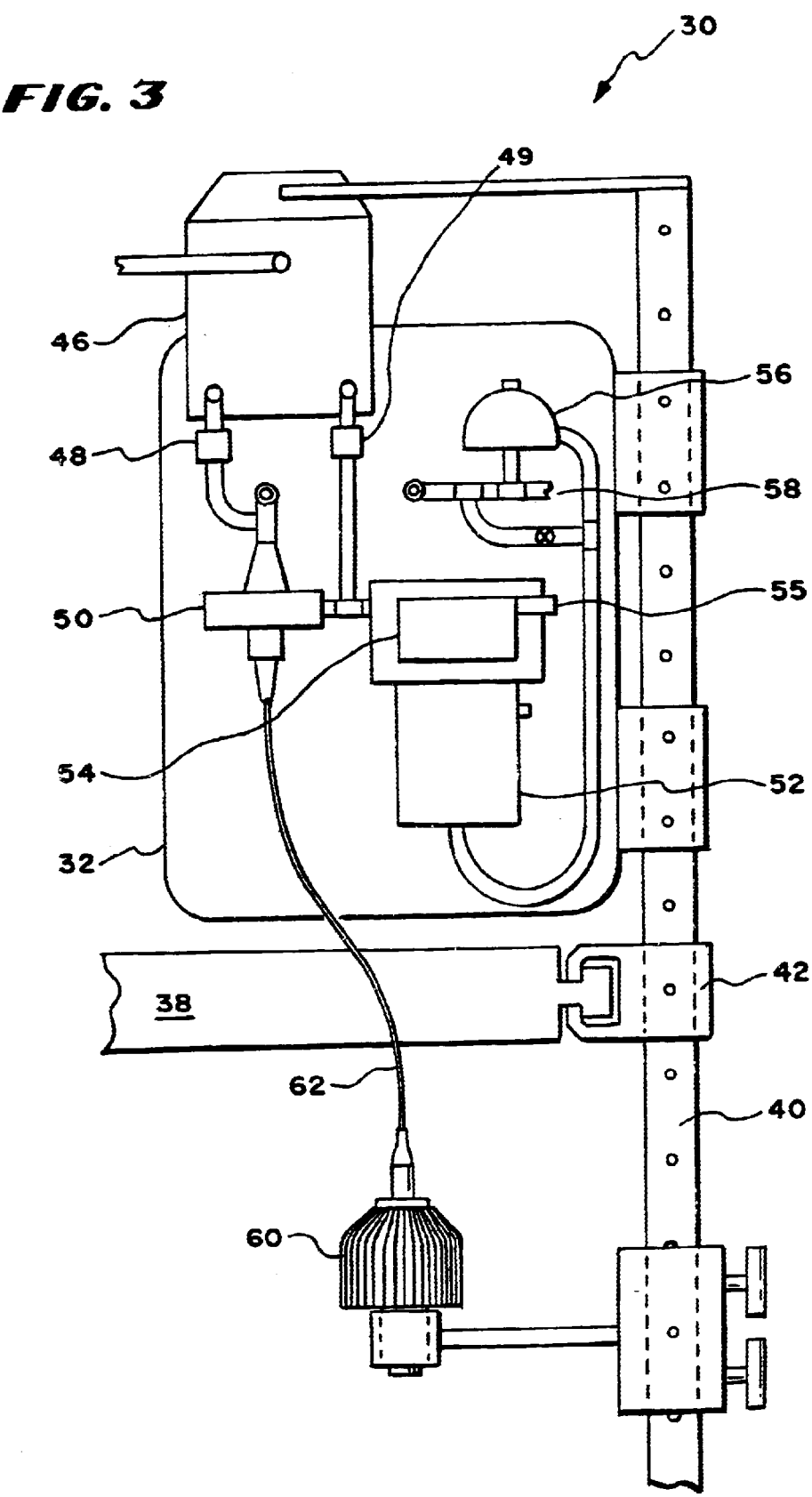
FIG. 3 is a side view illustrating an exemplary embodiment of the CPB integration panel of the present invention, employing a passive reservoir 46 on the venous side.

FIG. 3 is a side view of a CPB integration panel 30 according to one embodiment of the present invention shown in use over the surgical table 38 through the use of a vertical rail 40 coupled to a horizontal bed rail 42. The CPB integration panel 30 of the present invention includes the generally rectangular panel member 32 equipped with a passive reservoir 46 and associated pinch valves 48–49, a centrifugal blood pump 50, an oxygenator 52 and heat exchanger 54, an arterial filter 56, and a cardioplegia inlet 58. It is to be readily understood that, although referred to as a panel 32, this structure may take any suitable form to support the various CPB components in a consolidated fashion within or adjacent to the sterile field. For example, the panel 32 may comprise a structure having a single ply or thickness equipped with suitable mechanisms for attaching and maintaining the various CPB components. The panel 32 may also comprise a manifold or box-type structure having an enclosed area suitable for receiving or housing (totally or partially) various components of the CPB circuit and associated tubing. The panel 32 and other components may be formed via thermoforming or injection molding to accomplish the desired geometry.

It is also to be understood that the enumerated CPB components are not necessarily exhaustive of those capable of being supported by the panel 32. For example, oxygenator 52 (FIGS. 3–4) may be replaced by any of a variety of other oxygenators, including those commercially available and that shown and described below with reference to FIGS. 5–14 (forming part of the present invention). Similarly, it will be appreciated that certain of the CPB components may be eliminated altogether from the circuit (depending upon the application) without departing from the scope of the present invention. In any event, the panel 32 and CPB components are preferably equipped with quick-connect couplings to provide component modularity and ease of use in assembly and/or component replacement, as well as ease in coupling the CPB integration panel 30 to the venous cannula 12 and arterial cannulae 26.

The passive reservoir 46 serves to allow volume addition or subtraction from the patient, to account for variation in venous and arterial flows, and to allow for pharmaceutical addition to the patient intra-operatively. The passive reservoir 46 is preferably of softshell construction, and is implemented when a closed perfusion system is desired. When the perfusionist requests, the passive reservoir 46 can be brought into the circuit under the direction of the system controller 36 (shown generally in FIG. 2 and described in greater detail below). In so doing, the passive reservoir 46 temporarily becomes active within the system. Although a variety of reservoir control methods exist, two primary methods include: (1) Pinch clamps 48, 49 on the tubing between the reservoir 46 and circuit; and/or (2) A small roller pump (not shown) with solenoid activated engagement to direct flow between the reservoir 46 and circuit. Both methods may be electronically and/or electro-pneumatically controlled. Typical materials employed include a PVC softshell heat sealed bag, Polycarbonate USP Class VI molded connectors, and PVC tubing. USP Class VI rated materials such as polycarbonate, ABS, or acrylic may also be employed.

The passive reservoir 46 has four primary modes of operation. The first (so-called "normal" or "idle") mode of operation involves circulating the blood within the passive reservoir 46 to prevent clotting, such as when the patient neither requires the addition or withdrawal of blood volume. This is accomplished by opening slightly both pinch valve 48 and pinch valve 49. When this occurs, a slight flow will be drawn out of the passive reservoir 46 (through pinch valve 48) for introduction into the blood pump 50, while a corresponding slight flow will be redirected into the passive reservoir 46 (through pinch valve 49) following the outlet of the blood pump 50.

The second (so-called "volume addition") mode of operation is where the patient requires volume, such as due to excessive blood loss during surgery. To accomplish this, pinch valve 48 is opened under the direction of the system controller 36 at the request of the perfusionist. Volume enters the circuit through the inlet of the centrifugal pump 50 (after passing through pinch valve 48). Electronic level measurement may be employed to close the pinch clamp 48 before the reservoir 46 runs dry, preventing transmission of air to the patient. The speed of the centrifugal PUMP 50 may be decreased manually by the perfusionist or automatically by the system controller 36 in order to maintain a constant perfusion rate.

The third (so-called "volume reduction") mode of operation is where the patient requires reduced volume, such as to correct for high patient blood pressure. To accomplish this, pinch valve 49 is opened as directed by the perfusionist via the system controller 36. Volume enters the reservoir 46 from the outlet of the blood pump 50 (after passing through pinch valve 49). The speed of the centrifugal pump 50 may be increased manually by the perfusionist or automatically by the system controller 36 in order to maintain a constant perfusion rate.

The fourth (so-called "pharmaceutical introduction") mode of operation is where the patient requires the aid of pharmaceutical to be introduced into the blood supply. Under this mode, pinch valves 48 and 49 are opened fully as a given pharmaceutical agent is introduced into the blood supply within the passive reservoir 46. The controller 36 (at the request of the perfusionist) flushes and circulates this pharmaceutical agent into the blood supply of the patient. By opening up both pinch valves 48 and 49, the level of the reservoir 46 is maintained and the speed of the pump 50 is maintained.

The centrifugal pump 50 is cable driven from a remotely disposed motor 60, which is of key importance to positioning the CPB integration panel 30 within or closely adjacent to the sterile field. A cable drive 62 is preferably magnetically coupled to the motor 60 for separation of the motor 60 from pump 50, providing a multitude of mounting possibilities. A volute style centrifugal pump 50 is chosen for maximum pressure head from a minimum size pump, reducing total prime volume. One such centrifugal blood pump 50 is shown and described in commonly owned and copending International Patent App. Ser. No. PCT/US01/02531, filed Jan. 26, 2001, the entire contents of which are hereby expressly incorporated by reference into this disclosure as if set out fully herein. In the described circuit, the pump 50 output is directly connected to the inlet of the heat exchanger 54/oxygenator 52 to further reduce prime volume, although this is not a requirement. Pump speed and flow rate are directed and monitored by the main control console 36. With combined reference to FIGS. 2 and 3, the remotely placed control console 36 is electrically connected to the magnetic coupled motor 60. The control console 36 may be of the type shown and described in the aforementioned Int'l Pat. App. Ser. No. PCT/US01/02531. Various levels of automated control are possible from full manual to fully automated with manual fine-tuning override to customize system operation for the case at hand. The materials employed in the pump 50 may include all those suitable for biological applications, including but not limited to stainless steel, Rulon J, and USP class VI rated material such as polycarbonate.

Blood flow comes from the centrifugal pump 50 into the heat exchanger 54 where temperature of the patient can be raised or lowered based on procedural need by introducing hot or cold fluid (such as water) into and out of a heat exchanger port 55 in a known manner. The oxygenator 52 may comprise any number of suitable oxygenators, including those commercially available and those of a type shown and described below with reference to FIGS. 5–14. The heat exchanger 54 and oxygenator 52 depicted within the circuit preferably have a low prime volume with a round central flow path determined by the casting. Stainless steel or polymeric heat exchange capillaries are bonded or cast in place to prevent fluid communication between the heat exchange liquid and blood. In the case of a sterile field mounted system, an additional heat exchanger (not shown) may be required to prevent the flow of non-sterile fluid into the sterile field in the unlikely event a leak develops in the system. The oxygenator 52 may include any of a variety of readily available or later designed oxygenation materials, including but not limited to multiple layers of Membrana hollow fiber material folded or wound in any number of known or later-developed fashions. Cross flow of blood across the hollow fiber material promotes oxygenation through breakup of the blood film boundary layer. USP Class VI material such as polycarbonate is typically used for oxygenator structure construction. Oxygenation occurs through use of Membrana Oxyphan hollow fiber matte material. Heat exchange occurs through use of stainless steel tubing or polymeric capillary material disposed within the heat exchanger 54, such as HEX PET material manufactured by Membrana.

Blood flow progresses from the oxygenator 52 to the arterial filter 56. The arterial filter 56 serves to prevent air and foreign material transmission from the circuit to the patient. Most arterial filters have an air trap built in allowing removal of air through constant or periodic flushing of the trap line to the venous reservoir. Commercially available filters abound for this circuit. Low prime volume is key for effective implementation. In certain applications, it may be possible to eliminate the arterial filter 56 from the overall circuit, which is deemed within the scope of the present invention.

From the arterial filter 56 blood flows to the front side of the panel 32, which may be sterile, where cannulae or tubing connections maybe made. Preferably, these connections are carried out by employing quick-connect coupling features of the type shown and described in the aforementioned Int'l Pat. App. Ser. No. PCT/US01/02531. Traditional PVC or polyurethane cannulae are employed to develop blood flow between the patient and the CPB circuit. Such cannulae may be of the type shown and described in the aforementioned Int'l Patent Application.

Figure 4:
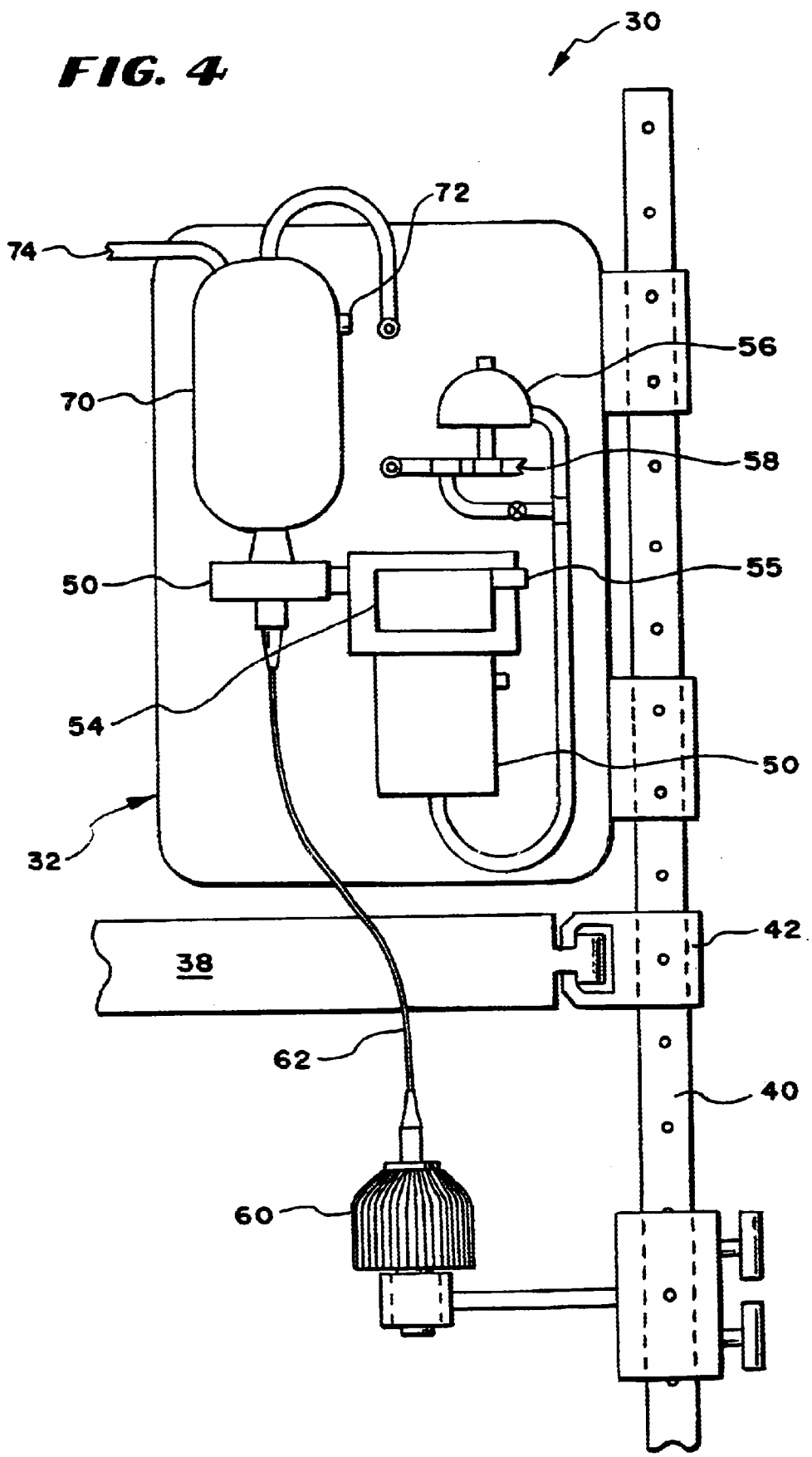
FIG. 4 is a side view illustrating an exemplary embodiment of the CPB integration panel of the present invention, employing a vacuum-assisted active reservoir 70 on the venous side.

FIG. 4 is a side view of a CPB integration panel 30 according to another embodiment of the present invention shown in use over the surgical table 38 through the use of vertical rail 40 coupled to the horizontal bed rail 42. The CPB integration panel 30 in this embodiment is similar to that shown in FIG. 3, with the exception of a vacuum assisted active reservoir 70. Accordingly, only the operation of the active reservoir 70 need be set forth below. Like the passive reservoir 46 described above, the vacuum-assisted active reservoir 70 is also on the venous side. The active reservoir 70 is preferably of the hardshell type. The main distinction between the active reservoir 70 and the passive reservoir 46 is that the active reservoir 70 remains in the primary flow path at all times. Venous blood is removed from the patient to the reservoir 70 located above patient level through use of a low level vacuum 72 connected to the hardshell reservoir 70. Blood flows from the patient into the entrance of the hardshell reservoir 70 where it encounters an internally disposed flow director (not shown). The flow director maintains a solid stream blood flow as the blood enters the reservoir 70 and eliminates dripping and/or foaming. Blood from a cardiotomy suction return 74 (pump suckers) is directed into the main flow channel where it is combined with the venous flow. All blood is then directed through Antifoam-A coated foam material and screen and/or depth filters to prevent foam development and prevent transmission of foreign debris back to the patient. Geometry in the outer casing promotes stream flow into the bottom of the reservoir 70 and prevents vortex formation of flow as it travels downward to the centrifugal pump 50. Filtration materials are typically made from nylon or polyester. Antifoam A coating is applied to polyester foam materials which are available various pore per inch ratings. The hardshell reservoir 70 and internal components are preferably made of USP Class VI rated materials such as polycarbonate, acrylic or polypropylene.

Figure 5:
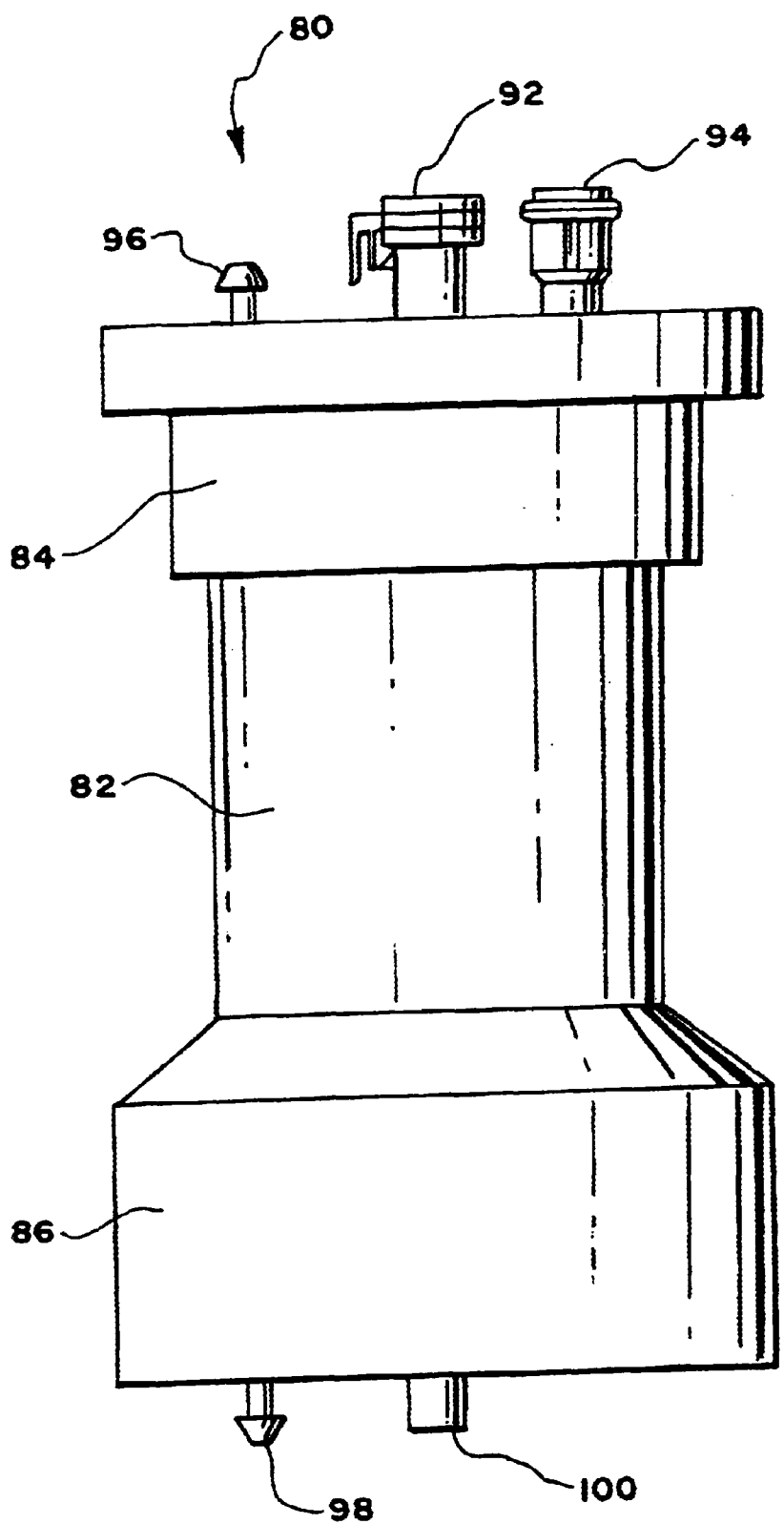
FIG. 5 is a side view illustrating an exemplary embodiment of an oxygenator of the present invention.

Referring to FIGS. 5–14, shown is an oxygenator 80 (forming part of the present invention) suitable for use as part of the CPB integration panel 30 described above with reference to FIGS. 1–4. Referring to FIG. 5, the oxygenator 80 of the present invention comprises an outer casing 82 extending between first cap 84 and second cap 86. With combined reference to FIGS. 5–7, outer casing 82 is adapted to house a hollow fiber membrane 88 disposed about inner core tube 90. First cap 84 includes fluid inlet 92, fluid outlet 94, and gas inlet 96. Second cap 86 includes gas outlet 98 and a rotor 100. Blood oxygenator 80 may optionally include a heat exchanger (not shown), a blood filter (not shown), and a de-bubbling chamber (not shown). Outer casing 82 comprises a generally cylindrical structure having first and second ends and a lumen extending therebetween. Outer casing 82 may be constructed of a biocompatible material such as polycarbonate, lexan or polyvinylchloride (PVC). Outer casing 82 further contains at least one aperture 102 disposed adjacent the second end.

Figure 11:
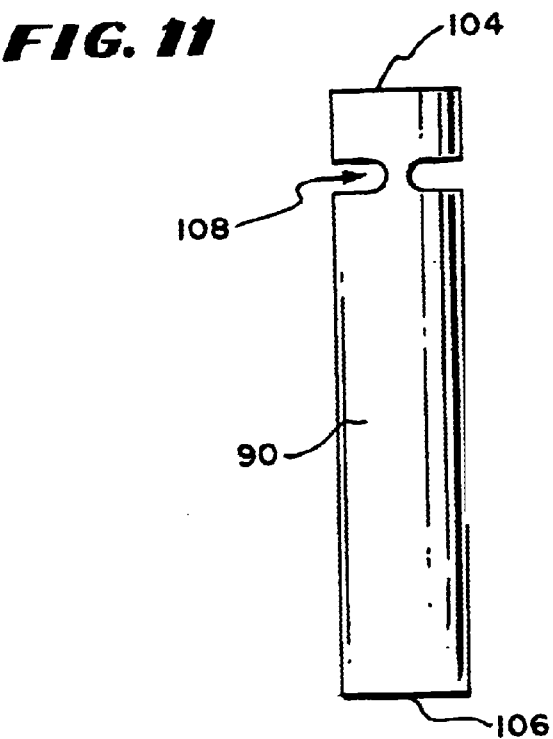
FIG. 11 is a side view illustrating the center core tube of the oxygenator of the present invention.
Figure 12:
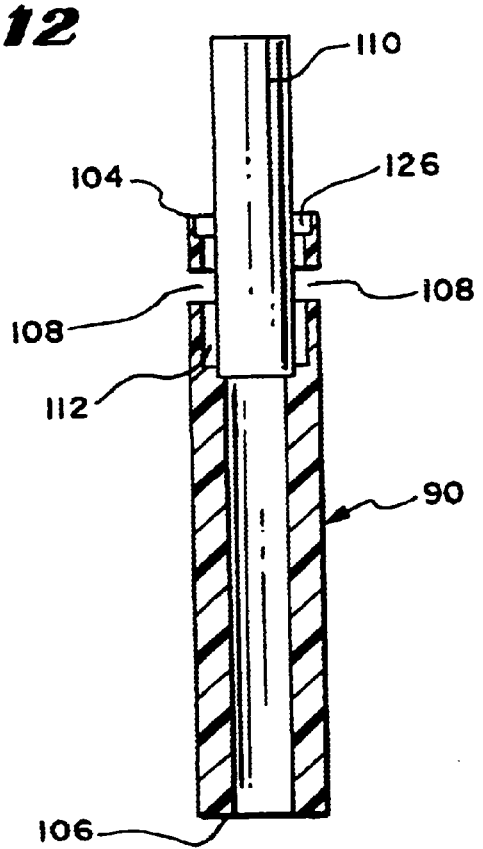
FIG. 12 is a partial cross sectional view of the core tube and conduit of the oxygenator of the present invention as assembled.

Turning to FIGS. 11–12, the inner core tube 90 comprises a generally cylindrical structure having a first end 104 and second end 106 and a generally cylindrical lumen extending therebetween. Inner core tube 90 further includes at least one aperture 108 disposed adjacent first end 104. Inner core tube 90 is adapted to receive one end of conduit 110. The lumen of inner core tube 90 has an area of increased diameter just above the union with conduit 110, thereby defining a chamber 112 between the outer diameter of conduit 110 and the inner diameter of conduit 70. Aperture 108 allows blood to flow into chamber 112 for delivery to blood outlet lumen 114 of first cap 84 as shown in FIG. 6.

Figure 14:
FIG. 14 is a side view of the membrane winding process for use in forming the oxygenator of the present invention.

During assembly of oxygenator 80 (see FIG. 7), a hollow fiber membrane 88 is disposed about inner core tube 90, the combination being dimensioned to be received within the inner diameter of outer casing 82. Hollow fiber membrane 88 may be formed in any number of known fashions, for example this may be accomplished by winding at least one hollow fiber 116 about the inner core 70 as shown in FIG. 14. In an alternative embodiment, the hollow fiber membrane 88 may be formed by disposing or winding a hollow fiber mat (not shown) about inner core tube 90. Such a hollow fiber mat may be constructed with individual hollow fibers 116 disposed in a substantially parallel fashion, or at an angle between 0 and 360 degrees as referenced to the direction of winding, such that the hollow fibers are not aligned with one another. Referring now to FIG. 6, the assembly of hollow fiber membrane 88 about inner core tube 90, the combination is disposed within the lumen of outer casing 82 creating Assembly 117. Assembly 117 is then placed in a machine whereby resin is injected into first end and second end and allowed to cure, thereby sealing hollow fiber membrane 88 to outer casing 82. After the resin has cured, the ends of the hollow fiber membrane 88 are cut, thereby opening the inner lumen disposed within each hollow fiber forming the hollow fiber membrane 88. When assembled between end caps 84–86, gas flows through the inner lumen of the fiber forming the hollow fiber membrane 88 while fluid flows around the exterior of these fibers.

Figure 6:
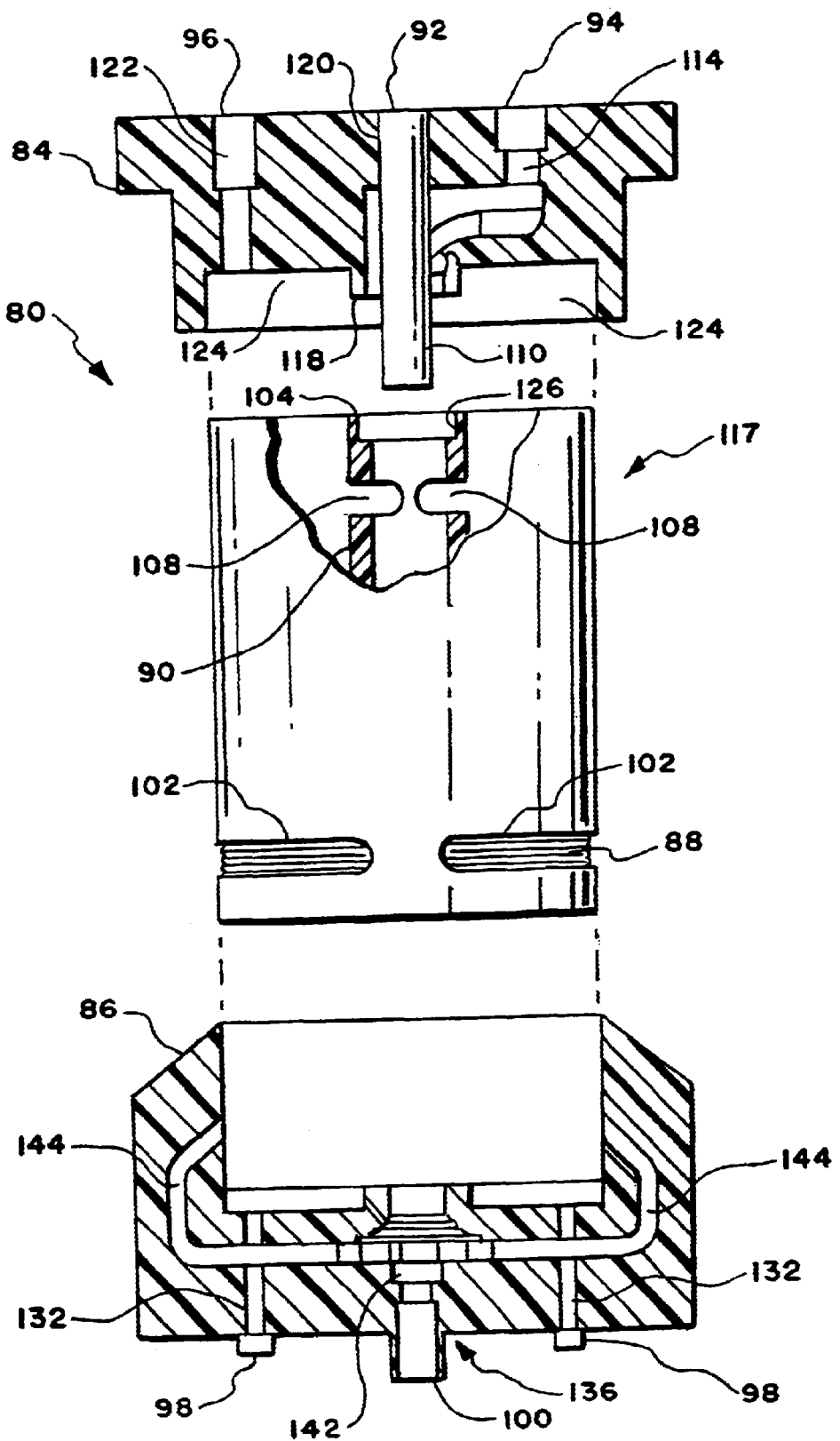
FIG. 6 is an exploded partial sectional view of the oxygenator of the present invention.
Figure 7:
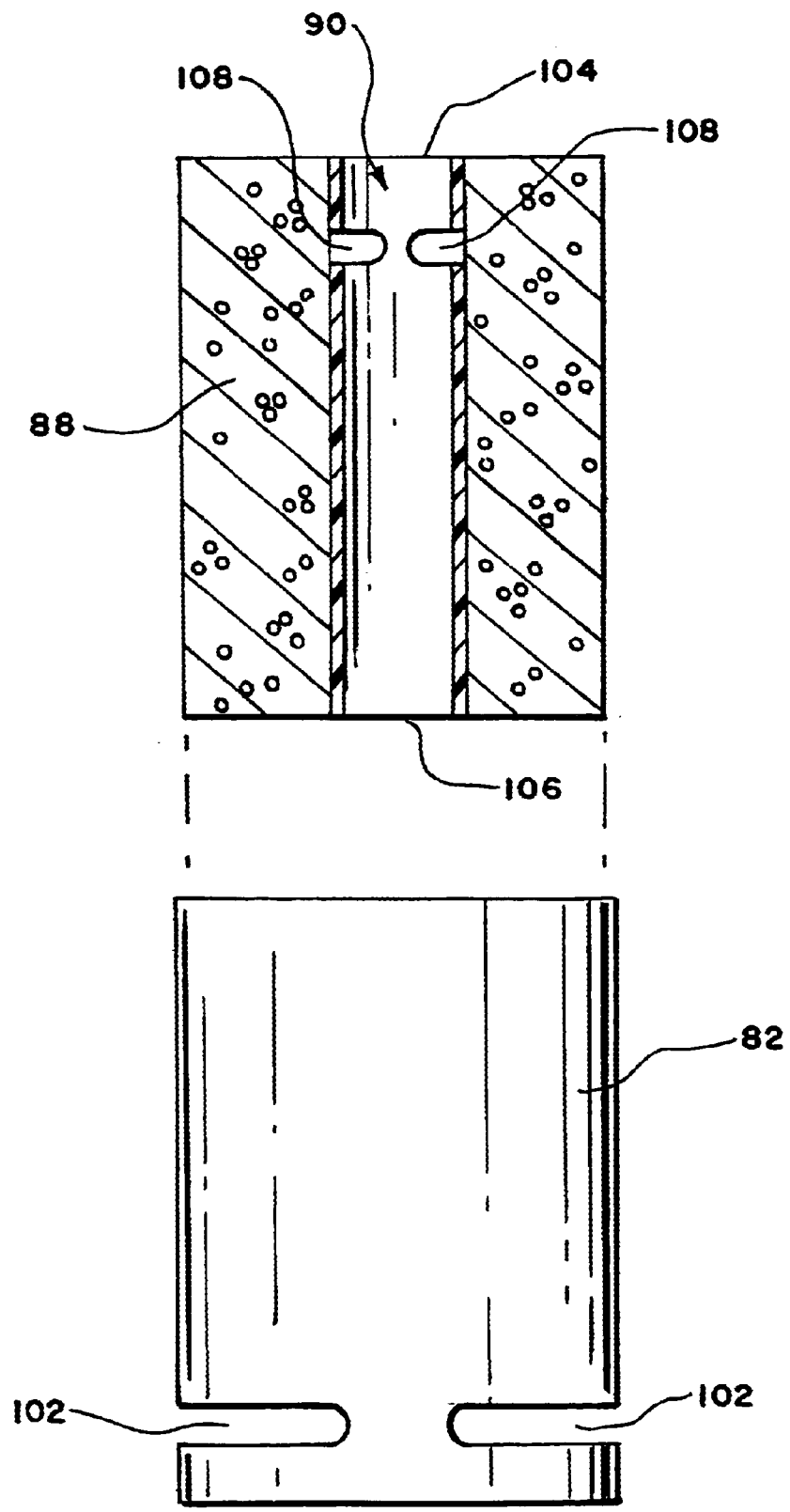
FIG. 7 is an exploded partial sectional view of the membrane prior to assembly into the outer casing of the oxygenator of the present invention.
Figure 10:
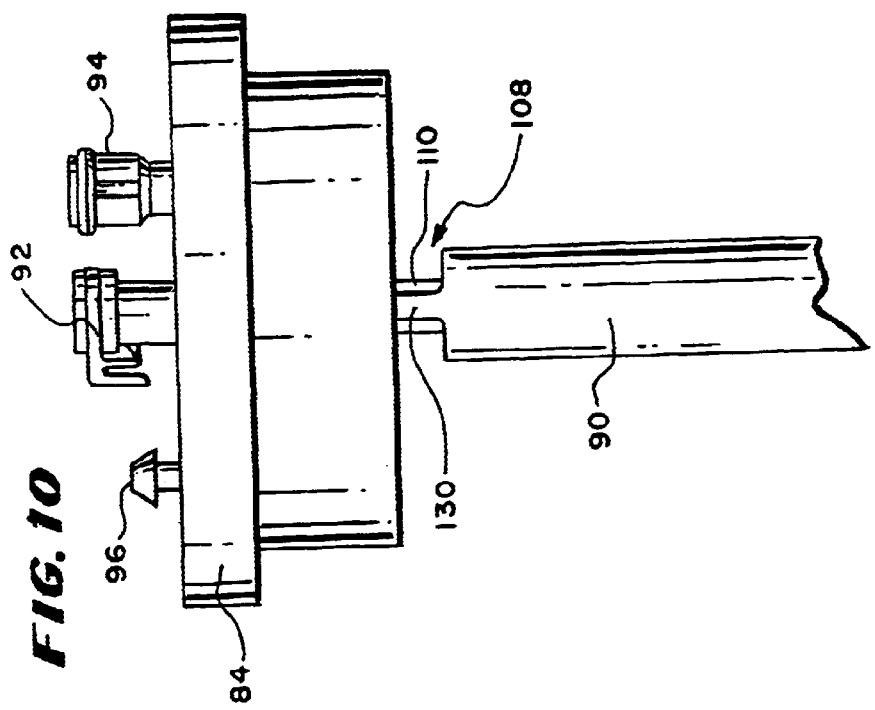
FIG. 10 is a side view illustrating the oxygenator cap and core tube of FIG. 9 as assembled.

With combined reference to FIGS. 5–6, first end cap 84 includes a flange 118, a blood inlet lumen 120, the blood outlet lumen 114, a gas inlet lumen 122 and a gas manifold 124. The blood inlet lumen 120 is in fluid communication with blood inlet 92 and conduit 110. The blood outlet lumen 114 is disposed in fluid communication with blood outlet 94. The gas inlet lumen 122 is disposed in fluid communication with the gas port 96. Flange 118 is dimensioned to receive annular ridge 126 of inner core tube 90. With combined reference to FIGS. 8 and 12, when assembled, blood inlet 92 is in fluid communication with the interior of conduit 110 and blood outlet 94 is in fluid communication with chamber 112 defined between the exterior of conduit 110 and a portion of the interior of inner core tube 90. Gas port 96 is in fluid communication with gas manifold 124 and the lumens of the hollow fibers forming the hollow fiber membrane 88. Alternatively, as shown in FIGS. 9–10, a flange 118 may extend from cap 84 to receive a tab 130 extending from first end 104 of inner core tube 90. In this configuration, flange 118 abuts tab 130 when assembled and thereby defines aperture 108.

Second cap 86 includes a gas outlet lumen 132, aperture 134, and pump assembly 136. The gas outlet lumen 132 is in fluid communication with the gas outlet 98. Aperture 134 is in fluid communication with the blood inlet 92 and the interior of conduit 110, and pump assembly 136 is in fluid communication with aperture 134, blood inlet 114 and conduit 110. The second cap 86 is dimensioned to receive the second end of outer casing 82. Pump assembly 136 comprises rotor 100, a sealing member 140 and bearing 142. Rotor 100 is rotatably disposed within second cap 86. Seal member 140 is disposed within second cap 86 and provides a seal between the fluid flowing within the second cap 86 and the exterior surface of second cap 86. Seal member 140 may be made of a biocompatible material such as silicone, urethane, rubber, latex or similar materials. Additionally sealing member 140 may include more than one sealing surface in communication with rotor 100. Although first cap 84 and second cap 86 are illustrated as unitary bodies, first cap 84 and second cap 86 may be assembled of multiple pieces.

In an alternative embodiment (not shown), first cap 84 may be dimensioned to receive the hollow fiber membrane 88, conduit 110, inner core tube 90, and second cap 86. In this embodiment, outer casing 82 is not required to support the hollow fiber membrane 88. The hollow fiber membrane 88 is potted with a bio-compatible resin and allowed to cure, thereby sealing the hollow fiber membrane to the inner core tube 90. After the resin has cured the ends of the hollow fiber membrane 88 are cut, thereby opening the inner lumen disposed within each hollow fiber forming the hollow fiber membrane 88. When assembled, the hollow fiber membrane 88 is disposed within the main lumen extending between the first cap 84 and the second cap 86.

Figure 8:
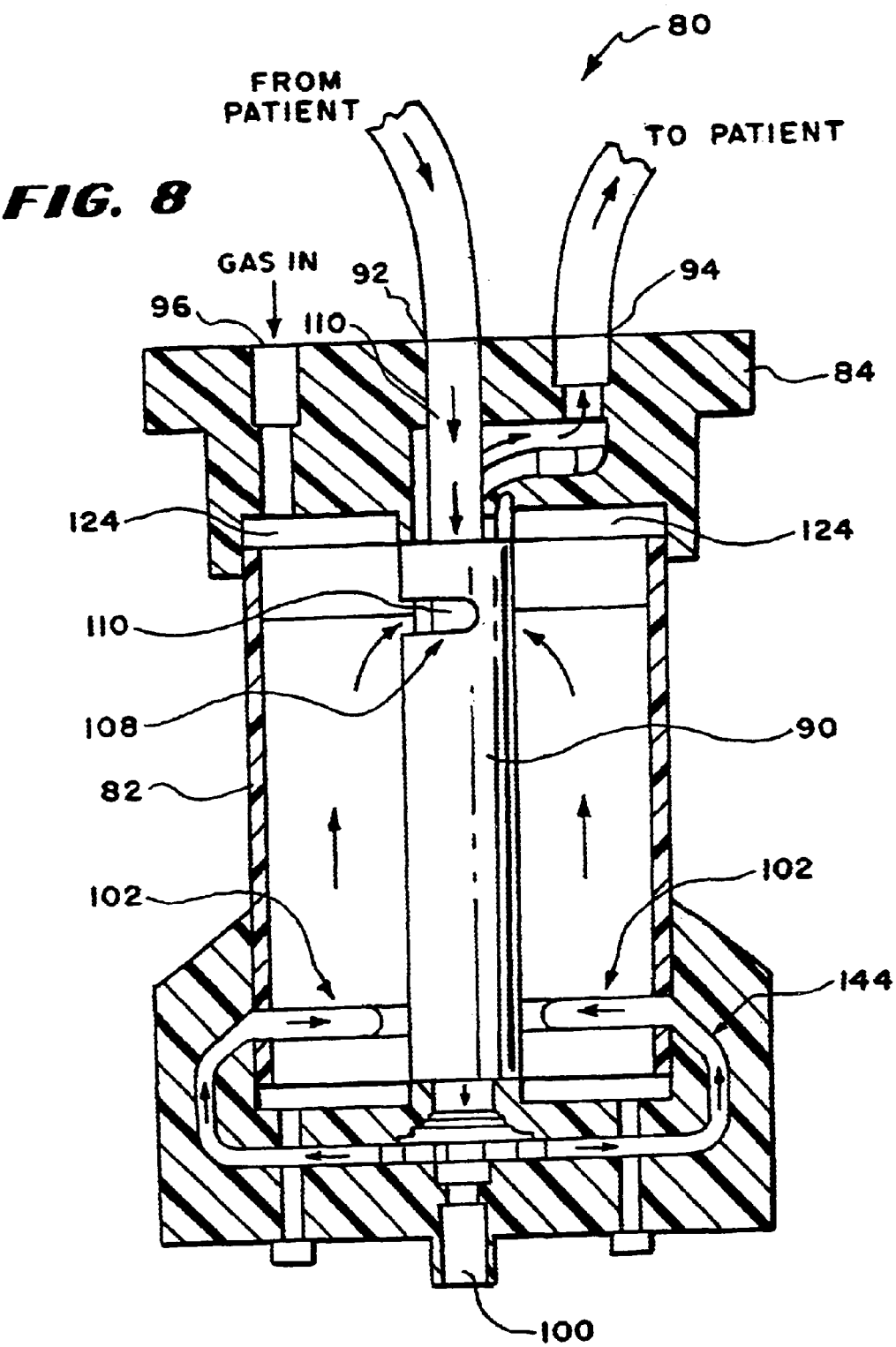
FIG. 8 is a cross sectional view of the oxygenator of the present invention assembled and illustrating the blood flow path.
Figure 9:
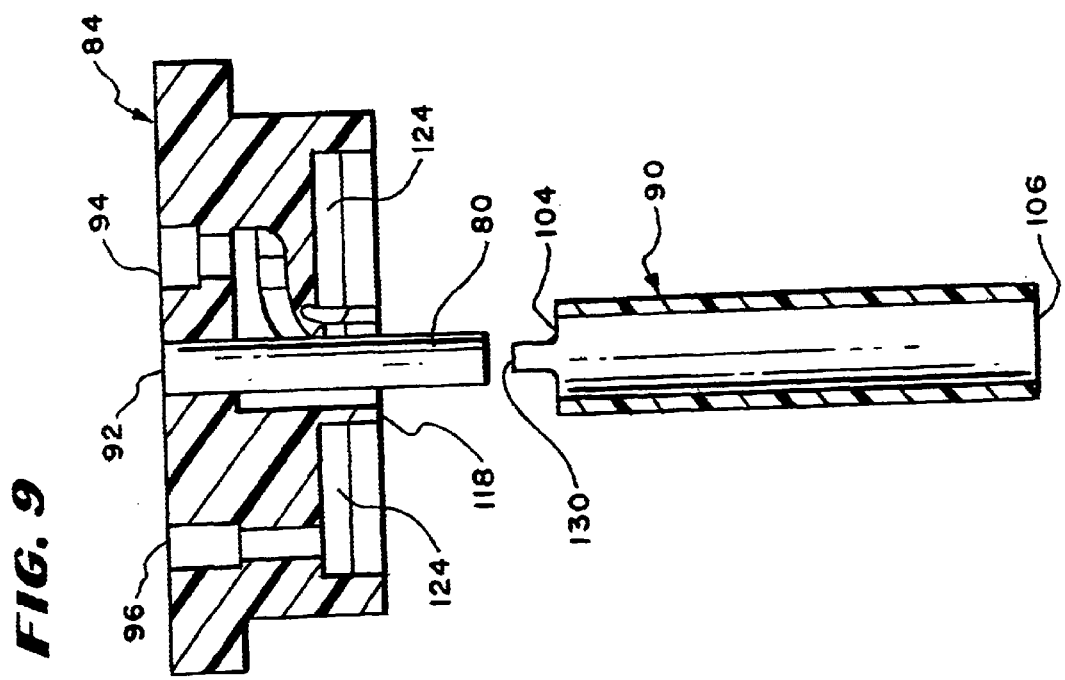
FIG. 9 is an exploded partial view of an alternative embodiment of the oxygenator cap and core tube of the oxygenator of the present invention.

As illustrated in FIG. 8, blood to be oxygenated is removed from the patient and routed to the fluid inlet port 45 under the pumping action of pump assembly 136. After flowing to the pump assembly 136 through conduit 110 and the interior of inner core tube 90, pump assembly redirects the blood flow through a channel 144 formed within the second end cap 50. The blood then passes through aperture 102 in outer casing 82, after which the blood flows around the exterior of the hollow fibers that make up the hollow fiber membrane 88. As the blood comes into contact with the surface of the hollow fibers carbon dioxide within the blood is exchanged with the oxygen flowing within lumens of hollow fibers. In a significant aspect of the present invention, pump assembly 136 serves to create secondary flows and/or induce eddies within the blood flowing through hollow fiber membrane 88. This advantageously decreases the thickness of the diffusion boundary layer that develops between the blood and the fibers within the hollow fiber membrane 88, thereby increasing the gas transfer between the blood and the hollow fiber membrane 88. The newly oxygenated blood then flows through aperture 108 in inner core tube 90 and into chamber 112 before passing out fluid outlet 94. The arrows in FIG. 8 represent the flow path of the blood through the oxygenator 80.

Figure 13:
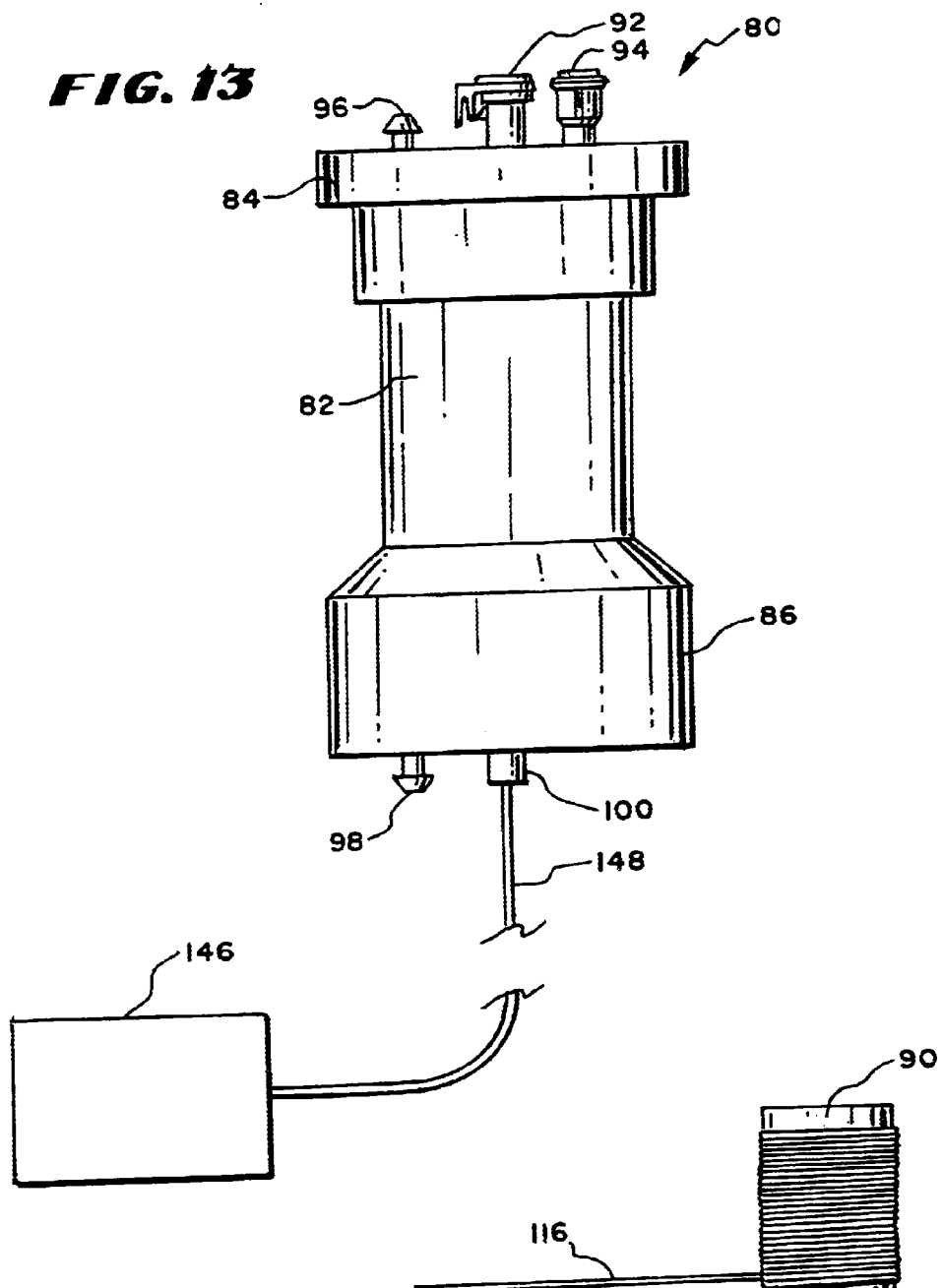
FIG. 13 is a side view of the oxygenator of the present invention coupled to a motor.

As shown in FIG. 13, a motor 146 may be connected to rotor 100 by a flexible drive shaft 148, thereby enabling oxygenator 80 to be placed within the surgical field. Alternatively, second cap 86 may further comprise motor 146 directly coupled to pump assembly 136 (not shown). In accordance with the present invention, the motor 146 may comprise any number of motor arrangements, including but not limited to an electric motor, an air powered pneumatic-type motor, and a fluid powered hydraulic-type motor.

FIG. 14 illustrates a method of forming a hollow fiber membrane 88 for use in an oxygenator of the present invention. Membrane 88 may be made by winding a hollow fiber 116 around an inner core tube 90. During the winding process, the winding pitch may be varied or the tension on the hollow fiber 116 may be increased or decreased. The spacing between the fibers can also be increased or decreased. As shown in FIGS. 5–13, membrane 88 and inner core tube 90 are then placed within the lumen of outer housing 82.

An exemplary use of the oxygenator 80 of the present invention is to provide oxygenation as part of the CPB integration panel 30 of the present invention. However, those skilled in the art will appreciate a wide variety of other uses for this oxygenator 80, including but not limited to use during beating heart surgery and other surgical procedures. The oxygenator 80 is advantageously sized such that it may be placed within the surgical field. In the preferred embodiment, the oxygenator of the present invention has an overall length between 3 and 12 inches, more preferably between 5 and 10 inches, and having an overall diameter between 2 and 10 inches, more preferably between 4 and 8 inches.

In summary, the CPB integration panel 30 of the present invention offers a host of significant improvements over traditional CPB circuits of the prior art. The miniaturization and consolidation of the CPB circuit dramatically reduces the prime-volume relative to traditional CPB circuits. For example, the CPB integration panel 30 of the present invention boasts a prime volume for neonatal and pediatric cases in the range of 100–225 ml (compared to 500–1000 ml for traditional CPB circuits), and a prime volume for adult cases in the range of 300–500 for adult cases (compared to 1500–2000 for traditional CPB circuits). In so doing, the CPB integration panel 30 of the present invention advantageously reduces hemodilution and its associated drawbacks. More specifically, it allows procedures to be performed at higher patient temperatures due to elevated hematocrit levels, and minimizes the need for, and cost involved with, additional blood transfusion, benefiting the patient and blood supply.

The CPB integration panel 30 of the present invention is also capable of being positioned at a higher vertical level than the patient, thereby reducing the risk of introducing air emboli into the patient. The CPB integration panel 30 also reduces the amount of field-recovered blood returned to the patient in cases with low to moderate blood loss, potentially reducing the risk of infarction associated due to debris initiated emboli within the patient. The CPB integration panel 30 of the present invention also minimizes the blood's exposure to foreign surfaces, which effectively reduces the risk of activating the blood's immuno-response system.

Those skilled in the art will recognize that various additions, modifications, deletions and alterations may be made to such preferred embodiments without departing from the spirit and scope of the invention. Accordingly, it is intended that any and all foreseeable modifications, additions, deletions and alterations to the described embodiments be included within the scope of the following claims.

What is claimed is:

1. A system for treating blood, comprising:
    a surgical drape dimensioned to be positioned at or near an operating table and having a first and a second side which, in use, define, respectively, a sterile operating field and a non-sterile field occupied at least in part by a patient's head,
    a panel adapted to be coupled to the drape and having a first side adapted to extend into the sterile operating field and a second side adapted to be coupled to at least one machine outside of the sterile operating field, and
    a plurality of blood treatment components disposed on the second side of said panel.

2. The system for treating blood of claim 1, wherein said plurality of components are coupled together to form a circuit having a prime volume between about 100–500 millimeters.

3. The system for treating blood of claim 1, wherein said plurality of components include at least two of an oxygenator, a passive reservoir, a blood pump, a heat exchanger, and a bubble trap.

4. The system for treating blood of claim 3, wherein aid oxygenator comprises a hollow fiber membrane oxygenator including a plurality of hollow fibers disposed within an outer casing, a fluid inlet and a fluid outlet disposed on respective ends of said hollow fibers, a gas inlet and a gas outlet, and a rotor in fluid communication with said fluid inlet.

5. The system for treating blood of claim 1, wherein said panel is located at or near operating table by being coupled to a vertical rail coupled to the operating table.

* * * * *